US00PP18738P3

(12) United States Plant Patent
Zwaan

(10) Patent No.: US PP18,738 P3
(45) Date of Patent: Apr. 22, 2008

(54) ***ACHILLEA* PLANT NAMED 'APRICOT DELIGHT'**

(50) Latin Name: *Achillea Millefolium*
Varietal Denomination: Apricot Delight

(75) Inventor: Michiel Zwaan, Alphen aan den Rijn (NL)

(73) Assignee: K. Sahin, Alphen aan den Rijn (NL)

( * ) Notice: Subject to any disclaimer, the term of this patent is extended or adjusted under 35 U.S.C. 154(b) by 218 days.

(21) Appl. No.: 11/348,934

(22) Filed: Feb. 7, 2006

(65) Prior Publication Data

US 2007/0186320 P1 Aug. 9, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Penny J. Aguirre

(57) ABSTRACT

A new cultivar of *Achillea millefolium,* 'Apricot Delight', characterized by it long blooming habit, its vigorous growth habit, its compact growth habit and its salmon pink flowers that fade to a light greyed-orange with consistent bloom color throughout the plant.

2 Drawing Sheets

Botanical classification: *Achillea Millefolium.*
Variety denomination: 'Apricot Delight'.

CROSS REFERENCE TO A RELATED APPLICATION

This application is co-pending with U.S. Plant patent application filed for a plant derived from the same breeding program entitled *Achillea* Plant Named 'Wonderful Wampee'. (U.S. Plant patent application Ser. No. 11/348,924).

BACKGROUND OF THE INVENTION

The present invention relates to a new and distinct cultivar of *Achillea* plant, botanically known as *Achillea millefolium* 'Apricot Delight' and will be referred to hereinafter by its cultivar name, 'Apricot Delight'. The new cultivar of *Achillea* is an herbaceous perennial grown for landscape use.

'Apricot Delight' was derived from a breeding program that focused on obtaining *Achillea* cultivars with a long blooming habit and flower colors that are resistant to fading. 'Apricot Delight' was selected in the summer of 2001 as a whole plant mutation that arose from repeated selections from seed originally sown of the seed strain *Achillea* 'Summer Pastels' (not patented) in Boskoop, The Netherlands.

'Apricot Delight' was selected as unique primarily for its sturdy stems, its compact plant habit and its salmon pink colored flowers. 'Summer Pastels', the parent strain, produces plants with variable plant habits and flowers with variable colors and color-fastness. 'Apricot Delight' differs from its closest comparison cultivar, *Achillea millefolium* 'Appleblossom' (not patented), in having a more compact plant habit and flowers that are salmon red in color versus pink. 'Apricot Delight' is more densely foliaged, has shorter stem internodes, and is shorter in height than 'Appleblossom'. 'Apricot Delight' is similar in bloom period and plant habit to 'Wonderful Wampee' from the same breeding program, however 'Wonderful Wampee' has clear pink flowers and is slightly taller.

Asexual reproduction of the new cultivar was first accomplished by basal cuttings in under the direction of the inventor in Lancaster, Pa. in September of 2002. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Apricot Delight' as unique from and all other varieties of *Achillea* known to the inventor.

1. 'Apricot Delight' is long blooming, blooming for about five weeks, typically from late June through July in Lancaster, Pa.
2. 'Apricot Delight' has salmon pink flowers that are consistent in color and fade to a light greyed-orange.
3. 'Apricot Delight' is densely foliated with thick dark green foliage on short internodes resulting in a compact plant habit.
4. 'Apricot Delight' has a vigorous growth habit.

BRIEF DESCRIPTION OF THE DRAWINGS

The accompanying colored photographs illustrate the overall appearance and distinct characteristics of the new *Achillea.* The photographs represents two year-old plants as field grown in Lancaster, Pa.

Figure 1:
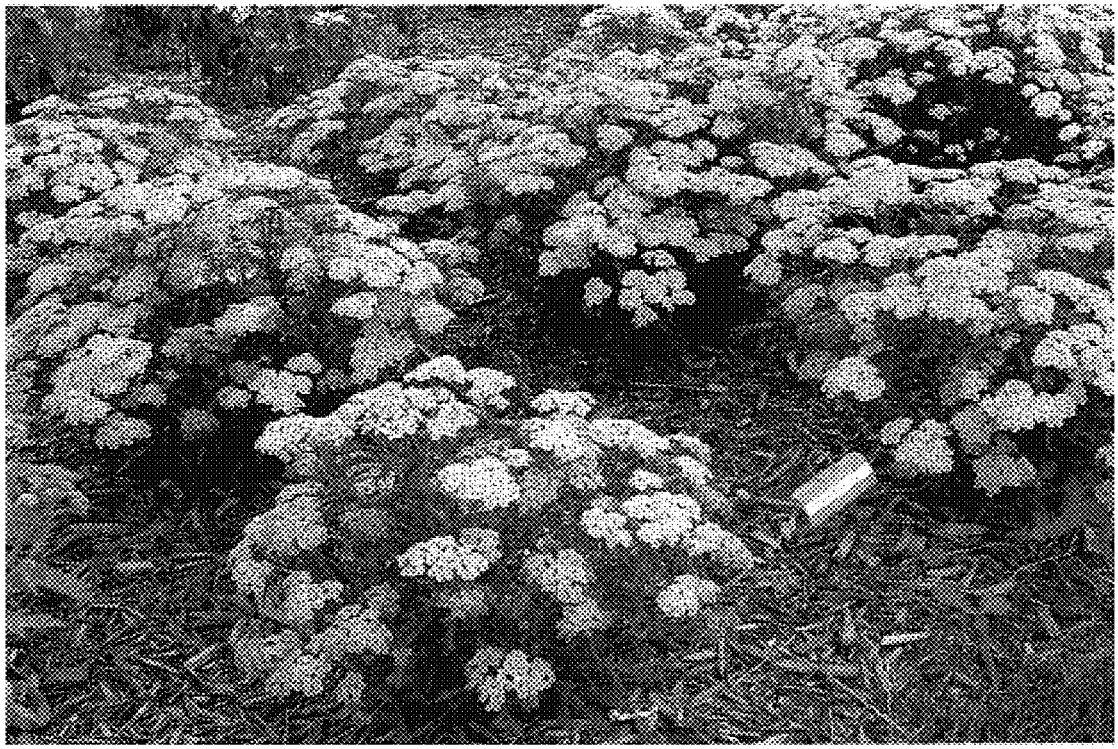
FIG. 1 is a photograph of a group of 'Apricot Delight' in bloom and shows the consistent and compact plant habit.
Figure 2:
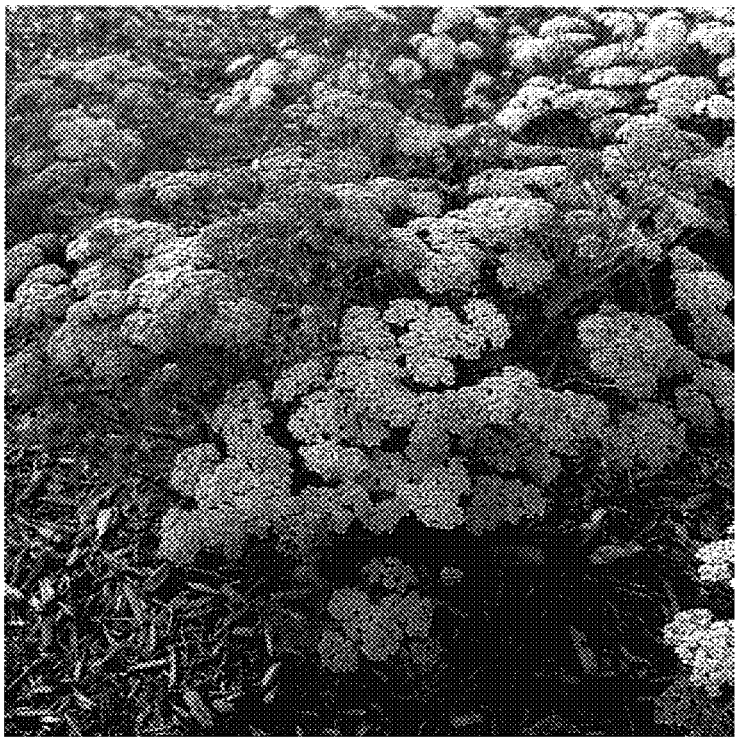
FIG. 2 is a photograph of a single plants of 'Apricot Delight'.
Figure 3:
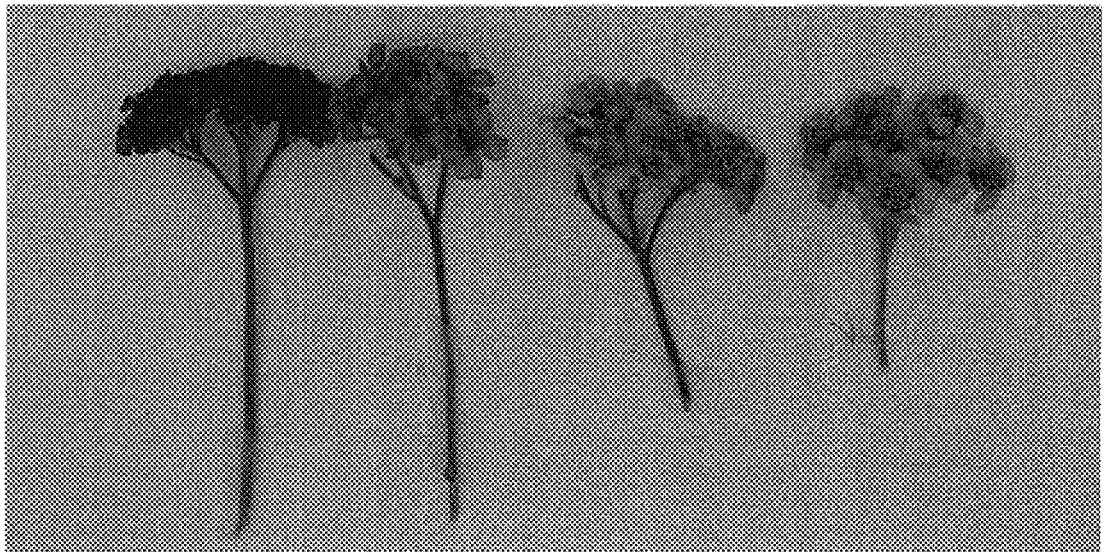

The photograph in FIG. 3 shows the progression of flower color with the newly opened flowers on the left and more mature flowers towards the right.

The colors in the photographs are as close as possible with the photographic and printing technology utilized. The color values cited in the detailed botanical description accurately describe the colors of the new *Achillea*.

DETAILED BOTANICAL DESCRIPTION

The following is a detailed description of the new cultivar as grown outdoors in for 12 weeks from a liner. The descriptions are based on observations over a period of two years in Lancaster, Pa. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

Botanical classification: 'Apricot Delight' is a cultivar of *Achillea millefolium*.

Parentage: Selection from *Achillea millefolium* 'Summer Pastels' (seed strain).

General description:

*Blooming period.*—Blooms for about 5 weeks, typically from late June through July in Lancaster, Pa.

*Plant habit.*—Herbaceous perennial, upright, mounded habit, strong flowering stems emerge from a basal rossette of foliage.

*Height and spread.*—Matures to about 33 cm in full bloom height and about 56 cm in width.

*Hardiness.*—U.S.D.A. Zones 4 to 8.

*Culture.*—Tolerant to a wide range of growing conditions, growing best in full sun in well-drained, moderately fertile soils.

*Diseases and pests.*—No susceptibility or resistance to diseases or pests common to *Achillea millefolium* has been observed for 'Apricot Delight'.

*Root description.*—Fibrous.

Growth and propagation:

*Propagation.*—Basal stem cuttings.

*Root initiation.*—Basal stem cuttings 8 cm in length dipped in 1000 ppm IBA and placed under mist root in about 10 days in a greenhouse kept at about 70° F. without supplemental lighting in spring and summer.

*Time required for root development.*—Rooted cuttings fully develop a 72-cell in about 4 weeks at 70° F. under mist, cells fully develop and flower in a six inch container in about 12 to 13 weeks when grown outdoors under natural lighting or when grown in a greenhouse at 68° F. without supplemental lighting and a constant liquid feed of 150 ppm N.

*Vernalization.*—Not required, vernalized plants flowers about 2 weeks sooner but unvernalized plants had better branching with more flowers.

*Crop maintenance.*—Plants can be cut back after the initial flush of flowers and rebloom occurs in about 4 weeks.

*Growth rate.*—Vigorous.

Stem description:

*Shape.*—Round, solid.

*Stem color.*—Between 144A and 144B. Stem size. About 3 to 4 mm in diameter, main branches up to about 35 cm in length.

*Stem surface.*—Glabrous with non-conspicuous fine white hairs and vertical ridges.

*Branching habit.*—Main branches emerge from tuft of basal foliage, typically 1 to 3 secondary branches emerge from nodes near apex, secondary branches about 10 to 16 cm in length, about 2 mm in diameter.

*Internode length.*—About 1 to 3 cm.

Foliage description:

*Leaf division.*—Simple, deeply dissected (fern-like).

*Leaf shape.*—Lanceolate, occasionally oblanceolate, leaf segments are ovate in outline.

*Leaf base.*—Blunt.

*Leaf apex.*—Acute.

*Leaf margin.*—Finely dissected. Leaf venation. Only midrib is visible, 144D in color.

*Leaf attachment.*—Sessile, clasping.

*Leaf arrangement.*—Basal foliage in rosettes, opposite on flowering stems, with 0 to 3 small leafs emerging from upper nodes.

*Leaf surface.*—Glabrous, upper and lower surfaces.

*Leaf color.*—Newly emerged basal foliage; upper and lower surfaces 144C, mature and emerging flowering stem foliage; upper and lower surfaces 137A.

*Leaf size.*—Basal leaves; up to about 26 cm in length, 3 cm in width with leaf segments up to 1.5 cm in length and 1 cm in width, leaves on flowering stems; 4 to 12 cm (typically 7 cm), about 1 cm in width with leaf segments about 1 cm in length and 0.5 cm in width.

*Foliage fragrance.*—None.

Flower description:

General description: Type. Compound corymb composed of numerous, capitulate, heterogamous with ray florets around the head margin and disk florets in the center, forming a radiant head.

*Lastingness of inflorescence.*—About 7 to 10 days until senescence of ray florets. Bracts and disk florets are persistent.

*Fragrance.*—None.

*Quantity of inflorescences.*—About 50 individual corymbs per flowering stem with about 15 to 20 capitula per individual corymb, and about 150 individual corymbs per flowering plant.

*Corymb size.*—About 8 cm in width and 5 cm in depth for terminal corymbs, average of 4 cm in width and 3 cm in height for side corymbs.

*Capitulum buds.*—About 4 mm in height and 2 mm in diameter, shape is ovate, color 139D with colored apex emerging 155B, changing to 158A with tips of buds 179A.

*Capitulum color.*—Overall color changes as ray floret color changes; from a salmon red (50B then 50C) to creamy pink (36A) and finally to a greyed-orange (N170D). Overall effect in fully bloom is multicolored.

*Capitulum size.*—About 1 cm in width and 8 mm in height.

*Peduncle.*—About 5 cm in length and 2 mm in diameter, 144B in color, texture is glabrous.

*Pedicel.*—About 5 to 7 mm in length and 1 mm in diameter, 144D in color, texture is glabrous.

*Receptacle.*—Not distinct, small, chaffy, 144A in color.

*Involucral bracts.*—Composed of a series of overlapping bracts, collectively 144B in color and form a cup (calyx-like) about 3 cm in width and 5 cm in height, individual bracts; about 4 mm in length, 1 mm in width, membranous, lanceolate in shape, acute apex, blunt base.

Ray florets (female): Number. 5.

*Shape.*—Orbicular portion on tube enclosing pistil.

*Aspect.*—Held flat.

*Size.*—7 mm in length and 4 mm width, showy, orbicular portion is 4 mm in length and width, tube portion is 3 mm in length and 0.4 mm in width.

*Petal apex.*—Rounded to blunt with 2 irregular notching, (sometimes tulip-like).

*Petal base.*—Rounded.

*Petal margins.*—Entire or notched on apex.

*Petal texture.*—Glabrous.

*Color.*—Upper and lower surfaces of petal: tube portion is 144C throughout development and not visible, showy orbicular portion changes from a salmon red (50B then 50C) with shadings of 50C in center of petal, to creamy pink (36A) with shadings of 50C near margins and finally to a greyed-orange (N170D) with shadings of purple (N78D).

Disk florets (bisexual):

*Quantity.*—About 20, densely packed in center of capitulum.

*Shape.*—Tubular, corolla is fused, flared at apex.

*Size.*—About 5 mm in length and up to 1 mm in width (flare).

*Color.*—Base (tube) is 144B to 144C in color, flared portion is translucent with a purple tinge on apex (84D), not distinct from ray flowers in color until the flower matures and the disk floret expand to a rounded mass (5 mm in diameter and 3 mm in height) and turn light lavender in color (84 D).

Reproductive organs:

*Presence.*—Disk florets are perfect with some functionally staminate, ray florets are carpellate.

*Gynoecium.*—1 Pistil, bifid stigma, translucent and light yellow to while in color (155B), extends just beyond the flare of disk florets and emerges at the junction of the tube and showy portion of the petal of the ray florets. Ovary is 1 mm in length, 0.3 mm in width, placement is inferior, translucent in color.

*Androcoecium.*—5 stamens, fused into tube surrounding style, anthers are 1 mm in length and about 0.3 mm in width, translucent, pollen is moderate in abundance and 9B in color.

*Fruit and seed.*—Fruit and seed set has not observed under the conditions tested.

I claim:

1. A new and distinct cultivar of *Achillea* plant named 'Apricot Delight' as herein illustrated and described.

* * * * *